US006599704B2

(12) United States Patent
Wagener

(10) Patent No.: US 6,599,704 B2
(45) Date of Patent: Jul. 29, 2003

(54) METHOD FOR DETECTING MUTATED ALLELES

(76) Inventor: Christoph Wagener, Department of Clinical Chemistry, UKE, Martinistrasse 52, 20251 Hamburg (DE)

( * ) Notice: Subject to any disclaimer, the term of this patent is extended or adjusted under 35 U.S.C. 154(b) by 0 days.

(21) Appl. No.: 09/849,901

(22) Filed: May 3, 2001

(65) Prior Publication Data

US 2002/0045227 A1 Apr. 18, 2002

Related U.S. Application Data

(63) Continuation-in-part of application No. 09/390,545, filed as application No. PCT/DE98/00676 on Mar. 4, 1998, now abandoned.

(30) Foreign Application Priority Data

Mar. 4, 1997 (DE) ......................................... 197 08 758

(51) Int. Cl.⁷ ............................. C12Q 1/68; C12Q 1/70; C12N 15/00; C12P 19/34; B01D 59/42
(52) U.S. Cl. ............................. 435/6; 435/5; 435/7.5; 435/7.7; 435/91.7; 435/91.2; 435/69.1; 204/450
(58) Field of Search .................... 435/6, 5, 7.5, 7.7, 435/91.7, 91.2, 69.1; 204/450

(56) References Cited

U.S. PATENT DOCUMENTS 5,352,578 A * 10/1994 Agrawal et al. ............... 435/6
5,496,473 A * 3/1996 Chow et al. ................ 210/635
5,512,441 A 4/1996 Ronai

FOREIGN PATENT DOCUMENTS

| EP | 0 461 496 A1 | 1/1991 |
| WO | WO 90/09393 | 8/1990 |
| WO | WO 93/22457 | 11/1993 |
| WO | WO 95/12689 | 5/1995 |

OTHER PUBLICATIONS

Nollau et al. J. Chromatogr. 1993, vol. 621, pp. 149–156.*
Abstract. XP–002079639. Tosoh Corp. Mutation detection of nucleic acid—by comparing factors lowering hybrid stability w.r.t. sample—and standard–nucleic acid of specific base sequence. Feb. 3, 1992.
Nollau et al. "Detection of K–ras Mutations in Stools of Patients with Colorectal Cancer by Mutant–Enriched PCR". *Int. J. Cancer*: 66, 332–336 (1996).
Khrapko et al. "A method for DNA sequencing by hybridization with oligonucleotide matrix". *DNA Sequence–I. DNA Sequencing and Mapping.* vol. 1, pp. 375–388. 1991.
Fodor et al. "Light–Directed, Spatially Addressable Parallel Chemical Synthesis". *Science*, vol. 251. pp. 767–773. Feb. 15, 1991.
Sidransky et al. "Identification of ras Oncogene Mutations in the Stool of Patients with Curable Colorectal Tumors". Science, vol. 256. Apr. 3, 1992, pp. 102–105.
Kuypers A. et al. J. Chromatogr. 1993, vol. 621, patent 149–156.
Debernardi S. et al Fron. In Bioscience. http://www.bioscience.org.
Peter N et al. JIFCC. 1997, vol. 9, patent. 162–170.
Parson B. et al Matat. Res. 1997, vol. 387, patent 97–121.
Webster's II New Riverside University Dictionary, patent. 93.
Dorland's Illustrated Medical Dictionary 28th edition, patent. 47.

* cited by examiner

*Primary Examiner*—James Housel
*Assistant Examiner*—Bao Qun Li
(74) *Attorney, Agent, or Firm*—Marianne Fuierer; Steven J. Hultquist; Yongzhi Yang

(57) ABSTRACT

A method for detecting mutated alleles in an excess of wild type alleles in a sample by isolating sample DNA; amplifying a target DNA sequence; and separating mutated DNA sequences from wild type DNA sequences by virtue of the preferential binding of the wild type sequences to carrier-bound complementary oligonucleotides. The amplification and separation steps may be iterated through one or more additional cycles to enhance sensitivity.

27 Claims, 6 Drawing Sheets

Fig. 1. Separation of mutated P53 allels from P53 wild type allels by separation chambers which are arranged in parallel and have immobilized oligonucleotides Fig. 2 Valve position in the serial arrangement of separation chambers Fig. 3: Separation of mutated P53 alleles from P53 wild type slleles by separation chambers which are arranged in series and have immobilized oligonucleotides.

METHOD FOR DETECTING MUTATED ALLELES

CROSS-REFERENCE TO RELATED APPLICATIONS

This is a continuation-in-part of U.S. patent application Ser. No. 09/390,545, filed 10-29-99 now abandoned, which in turn is a 35 U.S.C. §371 application based on international patent application PCT/DE98/00676 filed Mar. 4, 1998 and claiming priority of German patent application no. 197 08 758.2 filed Mar. 4, 1997. The disclosures of such applications are hereby incorporated herein by reference in their respective entireties.

FIELD OF THE INVENTION

The present invention relates to a method for detecting genetic modifications, particularly a method for detecting a few mutated alleles in an excess of wild type alleles.

BACKGROUND OF THE INVENTION

The detection of mutated alleles in an excess of wild type alleles offers a significant diagnostic potential. Illustrative fields of application include, for example:

(i) detection of tumor cells in the stool of patients suspected of having colorectal carcinomas;

(ii) detection of tumor cells in the sputum and bronchial lavage of patients suspected of having bronchial carcinomas;

(iii) detection of tumor cells in the urine of patients suspected of having bladder carcinomas; and (iv) detection of tumor cells in tissue biopsy samples.

The detection of mutant alleles of tumor genes in specimens such as urine, pancreatic juice, sputum, or stool holds great promise for an early diagnosis of cancer (Sidransky, D. (1997), "Nucleic acid-based methods for the detection of cancer," Science 278:1054–1059; Nollau, P. et al. (1996), Int. J. Cancer 66:332–336). In addition, the detection of mutant tumor genes in tissue samples such as lymph nodes or resection margins may allow a sensitive diagnosis of residual malignant disease. When few tumor cells are present with an excess of nonmalignant cells, mutant tumor alleles constitute a minor fraction compared to wild-type alleles, so that detecting point mutated alleles presents a major analytical problem. So far, this problem has been solved only when the point mutations in the respective tumor genes are known a priori.

Since K-ras is among the tumor genes most frequently mutated in human tumors, most experience in the aforementioned diagnostic applications has been obtained using this oncogene as a target. Various methods have been described for detecting mutant K-ras alleles in the presence of an excess of wild-type alleles. These methods include detection of cloned PCR products by allele-specific oligonucleotide hybridization (Sidransky, D. et al. (1992). Science 256:102–105); digital PCR (Vogelstein, B. and Kinzler, K. W. (1999), Proc. Natl. Acad. Sci. U. S. A. 96:9236–9241); allele-specific PCR (Smith-Ravin, J., England, J., Talbot, I. C., and Bodmer, W. (1995), Gut 36:81–86); a modification of the oligonucleotide ligation assay, termed Point-EXACCT (Somers et al. (1994), Nucleic Acids Res. 22:4840–4841; Somers et al. (1998), Biochim. Biophys. Acta 1379:42–52), mutant-enriched PCR (Chen and Viola, (1991), Anal. Biochem. 195:51–56; Kahn et al. (1991), Oncogene 6:1079–1083); and a modification of the latter making use of a thermostable restriction enzyme that is included in the PCR reaction and cuts any amplification products derived from the wild-type sequence (Fuery et al. (2000), Clin. Chem. 46:620–624).

Using these methods, only the well-calculated amplification of defined point mutations has heretofore been possible, it being necessary for this purpose to know precisely the location and identity of the point mutation. The allele-specific oligonucleotide hybridization of the cloned PCR products has not been suited to detect a few point-mutated alleles in an excess of wild type alleles when the position of the mutation, e.g., a point mutation or deletion, is not known in advance.

Therefore, it is an object of the present invention to provide a method for detecting and separating a few mutated alleles in an excess of wild type alleles.

SUMMARY OF THE INVENTION

The invention provides methods to achieve an enrichment of mutant alleles, by removing wild-type alleles by differential hybridization to carrier-bound complementary oligonucleotides whose sequences span the region of the gene in which point mutations are expected. The mutant sequences bind less tightly to the carrier-bound complementary oligonucleotides than do wild type sequences, and are separated therefrom and reamplified by PCR. By iterating this process, mutant alleles can be detected in the presence of an excess of wild-type alleles with high sensitivity.

The invention in one aspect relates to a method for detecting mutated alleles in an excess of wild typed alleles, comprising the separation of the wild type alleles by means of a separation process using a carrier to which one or several oligonucleotides complementary to the wild type alleles are bonded.

Another aspect of the invention relates to a method for detecting mutated alleles in an excess of wild type alleles in an examination sample, comprising the steps of:

isolating DNA from the examination sample;

amplifying from the isolated DNA a DNA sequence region that contains a target DNA sequence suspected of containing one or more mutations;

converting the amplified DNA sequence region to single stranded DNA; and separating mutated single stranded DNA sequences from unmutated single stranded DNA sequences by a separation step that employs preferential binding of the unmutated single stranded DNA sequences to one or more oligonucleotides; wherein the oligonucleotides comprise DNA sequences of 12 to 25 bases;

the oligonucleotide DNA sequences are complementary to DNA sequences in the unmutated target DNA sequence and together include all of the unmutated target DNA sequence; and the oligonucleotides are covalently bound to carrier materials.

The mutated target DNA sequence may contain one or more mutations such as point mutations, deletions, inversions, insertions, and substitutions. The separation step may be a chromatographic step, and the mutated single stranded DNA sequences may be selectively eluted from column-bound or carrier-bound oligonucleotides. The carrier or column material(s) to which the oligonucleotides are bound can be selected from the group consisting of glasses, gel materials, and polymer materials. The separation step may employ sense strands, antisense strands, or both. Sensitivity is enhanced when both sense and anti-sense strands are employed in the same separation vessel. In such a case, the oligonucleotide DNA sequences comprise at least one DNA sequence complementary to a sense strand and at least one DNA sequence complementary to an antisense strand of the amplified DNA sequence region.

The method is applicable to analysis of samples wherein the target DNA sequence is suspected of containing a point mutation. In that case, one oligonucleotide whose sequence is complementary to the unmutated target DNA sequence is employed.

For more complex analyses, the oligonucleotides may comprise a plurality of oligonucleotides having different sequences. Mutated single stranded DNA sequences may be separated from unmutated single stranded DNA sequences by preferential binding of the unmutated single stranded DNA sequences to the different sequence oligonucleotides by separation steps configured in series or in parallel flow arrangements.

In another aspect of the invention, referred to as subtractive iterative PCR (siPCR), mutant detection sensitivity is enhanced by employing one or more repetitions of the sequential steps of (a) amplifying the mutated single stranded DNA sequences obtained by separation from unmutated single stranded DNA sequences; and then (b) subjecting the amplified mutated single stranded DNA sequences to a separation step to remove residual unmutated single stranded DNA sequences, where the separation step employs preferential binding of the unmutated single stranded DNA sequences to one or more carrier-bound oligonucleotides. To obtain extremely high sensitivity, e.g., where the mutations are not known a priori, the one or more repeated separation step(s) employs a plurality of oligonucleotides having different sequences, and mutated single stranded DNA sequences are separated from unmutated single stranded DNA sequences by preferential binding of the unmutated single stranded DNA sequences to the different sequence oligonucleotides configured in a parallel flow arrangement.

In a further aspect, the invention relates to identifying a genetic modification in the mutated DNA sequences by methods such as size-sorting electrophoresis to show restriction fragment length polymorphism (RFLP).

In another aspect, the invention relates to a diagnostic method for detecting the presence of tumor cells in an examination sample obtained from a patient suspected of having cancer, e.g., carcinoma(s). The examination samples may comprise, without limitation, stool, sputum, bronchial lavage, urine, tissue biopsy material, saliva, or smear material. For example, the sample may be stool from a patient suspected of having colorectal carcinoma; a bronchial lavage sample from a patient suspected of having bronchial carcinoma; urine from a patient suspected of having bladder carcinoma; or pancreatic juice from a patient suspected of having pancreatic carcinoma.

Other aspects, features and embodiments of the invention will be more fully apparent from the ensuing disclosure and appended claims.

DETAILED DESCRIPTION AND PREFERRED EMBODIMENTS

Figure 1:
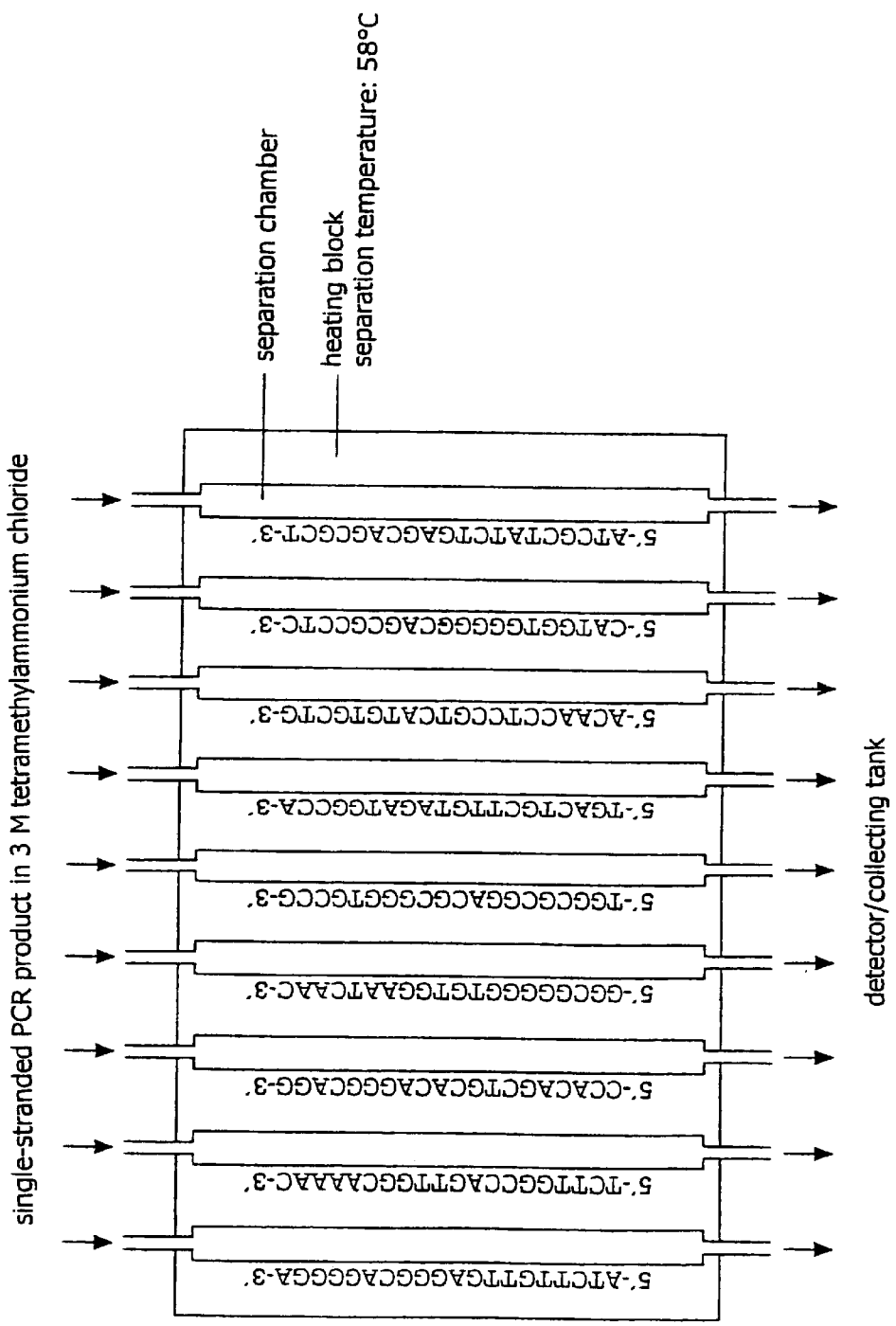
FIG. 1 shows a schematic flow-chart for separation of mutated p53 alleles from p53 wild type alleles using separation chambers arranged in parallel, with each chamber charged with carrier-bound oligonucleotides.

A "mutated allele," as compared to the wild type, results if point mutations, deletions, insertions, inversions and/or substitutions of relatively small to relatively large gene regions occur.

Examination samples that are suitable for testing for the presence of mutated DNA sequences comprise biological materials from a patient in need of diagnosis, e.g., blood, urine, stool, saliva, sputum, bronchial lavage, smear material, or biopsy material.

DNA is isolated from the examination samples. The region of interest may be amplified by PCR processes. The aspects of PCR amplification that should be considered when PCR is used as a step in a diagnostic test have been reviewed in detail by Neumaier et al. ("Fundamentals of quality assessment of molecular amplification methods in clinical diagnostics," Michael Neumaier, Andreas Braun, Christoph Wagener, Clinical Chemistry, 1998; 44:12–26). Further, it is advantageous in the practice of the invention to employ for PCR steps a polymerase with proofreading activity, e.g., Pfu polymerase.

The method of the invention advantageously employs a separation step that uses an allele-specific oligonucleotide hybridization. For this purpose, oligonucleotides, e.g., of 12 to 25, and preferably 16 to 20, base pairs (bp) are bound to a suitable carrier material. These oligonucleotide probes are complementary to sections of the wild type allele. The oligonucleotide probes are present in great excess as compared to the target mutated sequences.

Examples of suitable carrier materials to which the oligonucleotides can be bound include, without limitation: glasses, such as silicates; gel materials such as agarose and dextran; polymer materials such as polypropylene or polyacrylamide; and the like.

The oligonucleotides preferably are covalently bound to the carrier material. Methods of covalently bonding oligonucleotides to carrier surfaces are well-known; examples are described in Khrapko, K. R. et al., DNA Seq. 1, pp. 375–388 (1991); Fodor, S. P. A. et al., Science 251, pp. 767–773 (1991); and Maskos et al., Nucl. Acid Research 20, pp. 1639–1648 (1992).

Target DNA sequences from examination samples which contain both wild type alleles (in excess) and mutated alleles (few) are amplified and subjected to a separation process, for example chromatography or electrophoresis, via the carrier to which the oligonucleotides are covalently bound. Persons skilled in the art are familiar with conditions for carrying out such separation processes, and conventional separation apparatus, e.g., in the form of chromatographic columns, electrophoresis cabinets, electrophoresis tubes, capillaries, etc., can be advantageously used for such purpose. For the hybridization of the wild type allele with the carrier-bound oligonucleotide, the amplified DNA must be present as a single strand. This can be achieved by using buffer solutions having suitable salt contents, e.g., SSC or SSPE. The isolation of a DNA sense or antisense strand via a correspondingly labeled primer then is carried out. For example, when a biotin-labeled primer is used, the corresponding DNA strand can be isolated via binding to streptavidin beads.

The melting temperature of a wild-type specific oligonucleotide/wild type sequence hybrid can be estimated based on the number of hybridized base pairs (cf. Owczarzy, R., et al., "Predicting Sequence-Dependent Melting Stability of Short Duplex DNA Oligomers," Biopolymers (1998), 44:217–239). Hybridization is preferably accomplished at the estimated melting temperature of the hybrid of the wild-type specific oligonucleotide and its complementary sequence, and so mutant alleles predominantly remain unbound while wild-type alleles preferentially hybridize to the oligonucleotides.

Since the carrier-bound oligonucleotides are fully complementary only to the wild type sequences but not to the mutant sequences, they either hybridize with high selectivity with the wild type allele sequences or retard the mobility thereof in a selective manner. For the case of highly selective hybridization of the wild type, the mutated fragments are found in the sample fraction that is not bound to the carrier-bound oligonucleotides. In the second case of preferential binding of the wild type, the mutated fragments elute before the wild type fragments, and may be readily isolated therefrom.

The sensitivity of the method can be further increased if in addition to the sense strand of the wild type allele, the anti-sense strand is also employed in the separation step.

In one aspect of the invention, there is provided a method to detect point mutations. The methodologically simplest case is the case in which a mutant allele only has point mutations, and the sites where they typically occur are known. As an example, this situation pertains to the K-ras gene that in the case of colorectal carcinomas exclusively has mutations in codon 12 or 13. In this case, only one oligonucleotide of about 20 bases in length, which is complementary to the region of the wild type allele where codons 12 and 13 are located, must be synthesized. This oligonucleotide is covalently bound to a carrier that is suited for separation purposes, e.g., chromatographic or electrophoretic purposes. The gene of interest, here the K-ras gene, is isolated from the examination sample and labeled in the form of restriction fragments or PCR products that cover codons 12 and 13. Labeling can be accomplished by suitable means, for example, radionuclides, fluorescent dyes, biotin/avidin system labeling, etc. The labeled restriction fragments or PCR products are subjected to the chosen separation process.

Regarding the separation process, it is advantageous for the DNA to be present as a single strand. This can be achieved by, for example, by labeling one of the two DNA strands using biotin and isolating it by allowing it to bind to avidin (e.g., streptavidin beads; "Dynabeads" available commercially). If the wild type binds to the carrier-bound oligonucleotides with high selectivity, the mutated fragments will be found in the unbound fraction and can be analyzed after the elution and collection thereof. If the wild type binds preferentially, a buffer is used which elutes from the carrier the mutated fragment before the wild type fragment. Salt solutions and temperatures are selected such that the wild type allele is retarded compared with the mutated allele. A particularly suitable salt is tetramethylammonium chloride, since the stability of CG and AT base pairing is comparable. The temperature should be within the range of the melting temperature of the wild type allele. By way of specific example, when 20-meric bound oligonucleotides and 3.0 M tetramethylammonium chloride are used, the melting temperature of a fully complementary hybrid is 60° C.

In another aspect, the invention provides a method to detect genes with multiple heterogeneous point mutations. The p53 gene is an example; the p53 gene contains multiple mutations that are distributed over different exons. In order to detect multiple heterogeneous point mutations in a gene or a target sequence of interest, the following illustrative separation methodologies may be employed:

(i) a parallel arrangement of separation means, e.g., columns or capillaries, each charged with a separation material (carrier) to which a different wild type oligonucleotide has been bound;

(ii) a series arrangement of separation means, e.g., columns or capillaries, each charged with a separation material (carrier) to which a different wild type oligonucleotide has been bound; or (iii) the provision of a separation material (carrier) to which many different wild type oligonucleotides have been bound.

Parallel Arrangement of Separation Means

In one aspect of the invention, the oligonucleotides comprise a plurality of oligonucleotides having different sequences, and mutated single stranded DNA sequences are separated from unmutated single stranded DNA sequences by preferential binding of the unmutated single stranded DNA sequences to the different sequence oligonucleotides configured in a parallel flow arrangement. A plurality of separation materials (carriers) are provided for charging a plurality of separation means, e.g., columns or capillaries. To each separation material (carrier), a different wild type oligonucleotide is bound. The base sequence of each of these wild type oligonucleotides differs from all of the others used. If sense and anti-sense strands are to be analyzed for a given gene section, two carriers are provided to which are bound the oligonucleotides complementary to the sense or anti-sense strands, respectively. Each separation means is charged with a carrier to which a different wild type oligonucleotide has been bound. Sufficient carrier-bound oligonucleotides and separation means are provided to fully cover the entire region of interest in the wild type sequence.

For example, if oligonucleotides of 20 bp are employed, at least 30 separation means are provided to cover a region of 600 bp of a target wild type sequence. To obtain such a target sequence having 600 bp, after PCR amplification or corresponding restriction digestion of the allele being analyzed, the target sequence is converted by standard methods to a single strand sample and labeled by methods such as fluorescent dyes, radionuclides, the avidin/biotin system, etc. The 30 separation means are loaded in parallel with portions of the labeled sample, and the separation processes are carried out in parallel. The mutated allele is separated from the wild type allele, which exclusively or preferentially binds to the separation material (carrier). Because the labeled sample must be apportioned between the separation means, sensitivity is somewhat reduced in comparison to separation in series.

Series Arrangement of Separation Means

A plurality of oligonucleotide-bound separation materials (carriers) are provided for charging a plurality of separation means, e.g., columns or capillaries, as described hereinabove for parallel separations. The separation means, each of which is charged with a different oligonucleotide-bound carrier, are arranged in series. The labeled sample is loaded into the first separation means and successively eluted through the series of separation means. The series arrangement is useful when the wild type fragments bind to the carrier quantitatively, and the mutated fragments do not bind measurably. Valves are positioned between separation means in the series.

Depending on the position of the valve, a measuring cell (valve position I) or the next separation means (valve position II) is charged. The measuring cell is provided with analytic capability appropriate for sensing the labeled sample, such as, for example, a fluorescence photometer or a scintillation meter. The fragments are eluted by standard methods, e.g., heat or change of salt ion concentration. The separation process takes place as follows:

(a) valve downstream of separation means 1: position I
(b) charge separation means 1
(c) charge measuring cell with non-bound fraction
(d) valve downstream of separation means 1: position II
(e) valve downstream of separation means 2: position I
(f) charge separation means 2
(g) charge measuring cell with non-bound fraction and so forth.

The series arrangement provides high sensitivity.

Separation Materials Bearing Many Different Wild Type Oligonucleotides

Oligonucleotides complementary to various sections of the target wild type sequence may be bound to a single carrier. The buffer conditions must be chosen such that the wild type allele is retained preferentially to the mutated allele. This can be achieved when the separation is carried out at a temperature that is within the range of the melting temperature and that oscillates around the melting temperature. A reversible interaction between the carrier-bound oligonucleotides and the wild type sequences occurs under these conditions. The region of the gene having a point mutation is not retained. The interactions between the mutated alleles and the carrier-bound oligonucleotides are weaker than the interactions between wild type allele and the carrier-bound oligonucleotides.

Separation by a Subtractive Iterative PCR Process

In another aspect of the invention, an iterative method is provided that is based on the subtraction of wild-type alleles by hybridization to complementary oligonucleotides. The non-bound fraction is reamplified and resubmitted to a second round of subtraction of wild-type alleles by hybridization to complementary oligonucleotides.

This aspect of the inventive technique, termed subtractive iterative PCR (siPCR), is highly sensitive for detecting small amounts of mutated DNA sequences in biological samples. As an example, the siPCR method allows the detection of K-ras mutations in pancreatic juice with high sensitivity and reliability.

Figure 4:
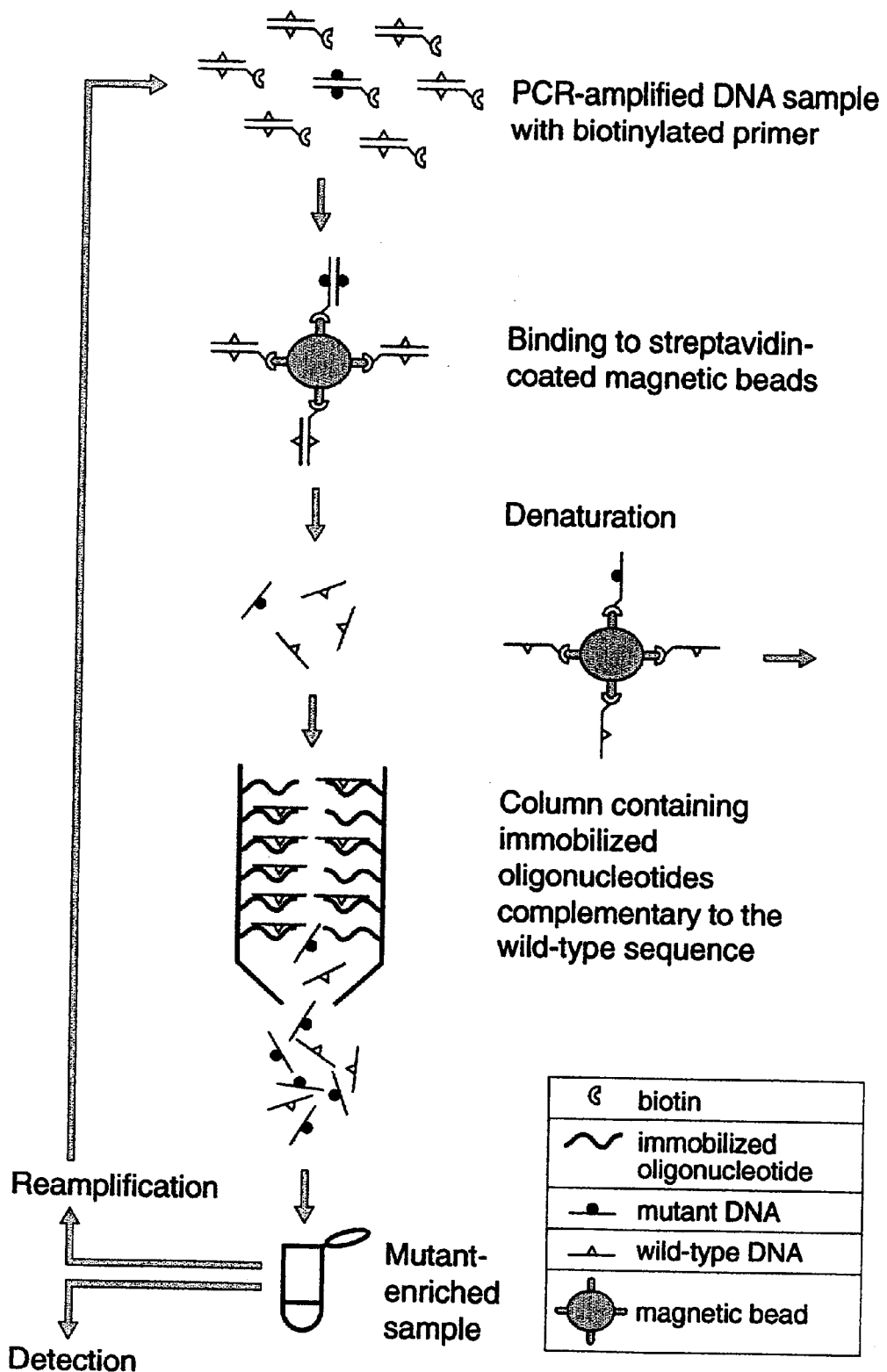
FIG. 4 shows a schematic representation of subtractive iterative polymerase chain reaction for detection of mutant DNA in the presence of wild-type alleles.

The principle of the siPCR technique applied for the detection of mutant K-ras alleles in pancreatic fluid is shown schematically in FIG. 4. The target sequence is amplified by PCR. Since one of the primers is biotinylated, ssDNA can be generated by binding the PCR product to streptavidin-coated magnetic particles followed by alkali denaturation. The ssDNA is loaded onto a chromatographic device containing column- or carrier-bound oligonucleotides that are complementary to the wild-type sequence. Wild-type DNA is retained on the column since it hybridizes to the immobilized oligonucleotides under stringent conditions. Mutated DNA sequences (alleles) are collected in the flow through, reamplified by PCR for another column run, or analyzed by DNA sequencing.

Iteration of the separation procedure significantly increases the sensitivity of the method. A second step of amplification and wild type subtraction results in a strong signal of the mutant DNA (see FIG. 5 below, Lane 2) that had barely been detectable after the first round of subtraction (Lane 1). Corresponding results were obtained with a point-mutated P53 allele (data not shown), indicating that the method performs with equal efficiency and discrimination for the detection of mutant alleles of different sequences. For example, samples with a mutant to wild-type DNA ratio of 1:1000 can be analyzed following by a process that includes two cycles of amplification and wild-type subtraction. In theory, by iterating this approach, the enrichment of mutant alleles increases exponentially with each round of the siPCR. The sensitivity of the assay is limited by the DNA polymerase error rate only.

In comparison with other methods aimed at the detection of mutant alleles in the presence of an excess of wild-type alleles, the siPCR protocol has distinct advantages. Detection of mutant PCR clones by allele-specific oligonucleotide hybridization, though a pioneering approach in the field, is laborious, technically demanding, and, for these reasons, not suitable for routine purposes. Allele-specific PCR requires multiple PCR primers complementary to the different oncogenic base substitutions. Digital PCR requires multiple PCR and hybridization reactions. Since single DNA molecules are amplified, DNA polymerase errors may present a problem. In contrast to these methods, few reagents are needed in siPCR, e.g., one set of primers and a device containing immobilized oligonucleotides. The siPCR method may additionally comprise DNA sequence analysis as a definitive method to confirm a specific base substitution.

Along with this detection method, the high fidelity of DNA amplification performed by using a polymerase with proofreading activity (Pfu polymerase) increases the specificity of a siPCR assay. In a number of investigations aimed at identifying mutant alleles, mutant-enriched PCR has been applied (Kimura W. et al., "Significance of K-ras codon 12 point mutation in pancreatic juice in the diagnosis of carcinoma of the pancreas," Hepatogastroenterology 46:532–539 (1999)). In contrast to the method of the invention, DNA polymerases with proofreading activity cannot be used in mutant-enriched PCR since the mismatch primers would be digested. In consequence, polymerase errors in the mutant-enriched PCR technique can produce base substitutions within the recognition site of the restriction enzyme and, in this way, may cause false positive results in the RFLP analysis when a high number of PCR cycles is performed to reach maximum sensitivity (Nollau and Wagener, 1997).

The siPCR method may be extended to the detection of other mutations not known a priori, by employing multiple parallel devices with immobilized complementary oligonucleotides covering the sequence range of a gene in which mutations are expected, as described hereinabove and shown in FIG. 1. After passing through the parallel columns, the non-bound fractions are pooled, reamplified, and submitted to a second absorption step. The number of iterative steps will depend on the available sample size and the sensitivity desired.

The present invention is distinguished in that a few mutated alleles can be detected in an excess of wild type alleles. Furthermore, the method of the invention is suited to detection of heterozygous and homozygous mutations and polymorphisms. The present invention provides a method capable of analyzing genetic modifications of diverse origin and such method is broadly useful for diagnosis. Furthermore, the method of the invention may be used for the development of new therapeutic approaches.

Various features and advantages of the invention are further illustrated by the following non-limiting examples.

EXAMPLE 1

Analysis of a Mutation in the K-ras Gene

DNA can be extracted from tissues, body fluids, secretions or excretions. For this purpose, samples such as stool, blood, pancreatic juice, urine, or sputum are suspended in an aqueous solution of 6 M guanidinium isothiocyanate. Following centrifugation, NP-40 is added (final concentration 1%). After an incubation period of at least 10 minutes at room temperature, 500 microliters of the suspension is fed into a commercially available cartridge having a glass filter to isolate the DNA. After centrifugation and two wash steps using cold ethanol (4° C.), the DNA is eluted with hot water (70° C.). In order to prevent degradation, any prolonged storage is in 10 mM Tris-HCl (pH 7.4).

For carrying out a PCR amplification, 500 ng DNA are transferred into 100 microliters of a 10 mM Tris-HCl buffer, pH 8.3. The buffer contains the following additions: 1.5 mM $MgCl_2$, 50 mM KCl 0.01% (w/v) gelatin, in each case 200 $\mu$M dNTP, 2.5 U Taq polymerase and 0.3 $\mu$mol of the respective primers. The sequence of the primers is as follows:

sense: 5'-GTATTAACCTTATGTGTGACATGTTC-3'; (SEQ ID NO. 1)

anti-sense: 5'-TCAAAGAATGGTCCTGCACC-3'. (SEQ ID NO. 2)

For concluding the oligonucleotide synthesis in an automatic DNA synthesizer, a biotinylated nucleotide is introduced into the anti-sense primer at the 5' end and a nucleotide labeled with a fluorescent dye (e.g. fluorescein) is introduced into the sense primer at the 5' end thereof. Such labeled nucleotides are readily commercially available.

For the detection of mutations in codons 12 and 13 of the K-ras gene, a 20-meric oligonucleotide is synthesized to solid carriers and linked to solid carriers, respectively. The sequence of the oligonucleotide is as follows:

5'-GCCTACGCCACCAGCTCCAA-3'. (SEQ ID NO. 3)

The solid carriers useful for such purpose include carriers suitable for chromatographic and electrophoretic separations. Glass and polyacrylamide are useful separation media, by way of illustration.

For example, porous beads are suitable as glass carriers. The glass surface is derivatized according to conventional methods, and the oligonucleotides are synthesized directly on the derivatized glass surfaces in an automatic DNA synthesizer (Applied Biosystems) in accordance with the manufacturer's instructions. For the purpose of derivatization, the glass beads (10 g) are incubated in 40 ml xylene+12 ml (3-glycidoxypropyl) trimethoxysilane having a trace of Hoenig base at 80° C. for about 12 hours. After washing in methanol and ether, the beads are dried in air and in vacuo. In a second step, alkyl spacer molecules were linked to the derivatized surface. For this purpose, the beads are fed for example into pentaethylene glycol. After washing in methanol and ether, the beads are dried in air and in vacuo. The beads then are stored in argon at −20° C. (Maskos U. & Southern EM. Nucleic Acids Res. 10, 1679–1684 (1992)).

The glass beads derivatized in this way are inserted directly into the DNA synthesizer.

For linkage to polyacrylamide, a methyluridine base is introduced at the 3' end in the oligonucleotide synthesis. Hydrazine groups are introduced into the polyacrylamide gel by treatment with a 50% aqueous hydrazine hydrate solution (1 h, at room temperature). For the purpose of linkage, the ribose at the 3' end of the oligonucleotide is oxidized with sodium periodate. The resulting aldehyde group is bound to the derivatized gel (Khrapko K. R. et al., DNS Seq. 1, 375–388 (1991)).

In order to prevent rehybridization of the single DNA strands in the course of chromatography or electrophoresis, it is useful to provide single-stranded DNA for the isolation. For this purpose, the primer in the anti-sense strand is biotinylated. The PCR product is heated and passed through a solid streptavidine phase (e.g. dynabeads). In this way, the anti-sense strand is removed. If the anti-sense strand is to be analyzed, the sense strand can also be removed by a corresponding biotinylated primer.

The wild type and amplificates mutated in codons 12 and 13, respectively, of the K-ras gene are isolated, for example by column chromatography or capillary electrophoresis (acrylamide gel filling of the capillaries). When the carrier is charged, buffer and temperature conditions are chosen such that the melting temperature is above that of mutant alleles and below that of wild type alleles. For example, SSC or SSPE in corresponding concentration (5–4×) and 3 M tetramethylammonium chloride, respectively, are suitable for use as buffers. A constant temperature separation means is provided by a heating block (e.g., maintaining a temperature of 58° C. when 20-meric oligonucleotides and tetramethylammonium chloride solution are used).

The fluorescence-labeled amplificates are detected by means of laser-induced fluorescence, for example by using an argon lif detector. For the sensitive detection of the DNA it is also possible to add a second PCR step.

EXAMPLE 2

Detection of Point Mutations in the $5^{th}$ Exon of the P53 Gene

The DNA is isolated as described in Example 1. The following primers are used for the amplification of the $5^{th}$ exon:

Sense: 5'-TTTCAACTCTGTCTCCTTCC-3'; (SEQ ID NO.4)

Anti-sense: 5'-AACCAGCCCTGTCGTCTCTC-3'. (SEQ ID NO.5)

Since the primers are present in introns, the entire sequence of exon 5 can be analyzed. The anti-sense sense primer is labeled with a biotinylated oligonucleotide at the 5' end, and the sense primer is labeled with a fluorescence-labeled oligonucleotide at the 5' end. PCR is carried out as described above. The biotinylated DNA strand is separated by bonding to immobilized streptavidin.

(a) Separation by Separation Means Arranged in Parallel

The separation means include columns having a separation medium such as glass beads or polyacrylamide (see FIG. 1). A 20-meric oligonucleotide is covalently bound to the separation medium in a specific column, as described above. The oligonucleotide is complementary to a given section of the DNA of exon 5 of the p53 gene. The oligonucleotides bound to the separation medium in the various columns cover the entire sequence of the 5$^{th}$ exon as a whole (see FIG. 1). The columns are disposed in a heating block to ensure a constant temperature.

The temperature for the separation of wild type and mutated alleles is 58° C. The columns are equilibrated with 3 M tetramethylammonium chloride solution. The PCR product to be investigated, which contains wild type and mutated alleles, is also dissolved in this solution. The PCR product is single-stranded (sense strand) and fluorescence-labeled. It is applied in aliquots to the columns. The mutated allele has a mismatch with respect to the oligonucleotide in the third separation chamber from the left. The mutated allele is present in a much lower concentration than the wild type alleles. The wild type alleles are bound in all of the columns. The mutated allele passes the third column from left, and is detected by the fluorescence signal.

The columns or detector can be movable. Prior to the charge of a particular column, the detector is connected with the outlet of the column. After the conclusion of the reaction, the detection is connected with the next column. By this approach, the fluorescence signal of a certain column and the mutation can thus be attributed to a defined section of the DNA sequence. This enables the well-calculated detection of a mutation after a second PCR; e.g. by allele-specific oligonucleotide hybridization or DNA sequencing.

(b) Separation by Separation Chambers Arranged in Series

Figure 2:
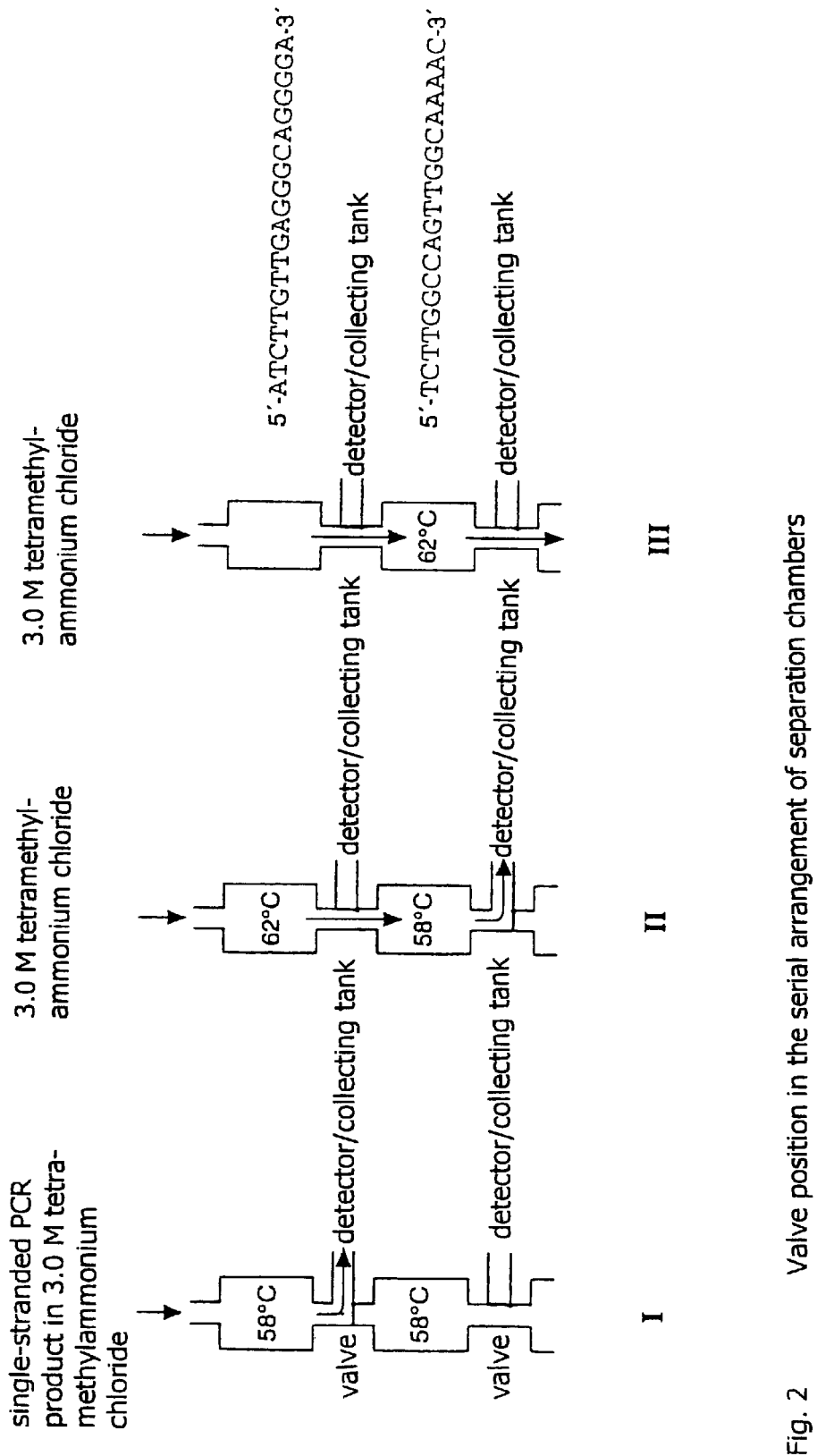
FIG. 2 shows schematically the valve positions used in a series arrangement of separation means.

A column chromatographic separation employing separation chambers arranged in series is provided. As described above in the preceding section (a), the individual columns are filled with a separating fluid to which one defined oligonucleotide is bound per column. Taken together, the oligonucleotides bound in the various columns cover the entire sequence of exon 5. The columns are temperature-controlled. In the case of the series arrangement, a valve is disposed between the individual columns. Charge and valve position are illustrated by the diagram in FIG. 2. The oligonucleotides bound to the separating matrix are shown on the right. Fluorescence labeling, isolation of the single-stranded DNA, as well as columns and sample solution, respectively, are as described in the preceding section (a).

Before the sample is introduced, the valve between columns 1 and 2 closes the inlet to column 2 and opens the inlet to detector or collecting tank (position I). The temperature in column 1 is 58° C. The single-stranded PCR product passes through column 1. Wild type DNA is bound. If a point mutation is present in the DNA section of the mutated allele, which is complementary to the bound oligonucleotide, the mutated allele will not be bound and will instead pass to the detector and collecting tank. If the point mutation is present in another DNA section, the mutated allele will also be bound.

After the conclusion of the reaction, the valve position between columns 1 and 2 is changed such that the inlet to column 2 is released and the outlet to detector/collecting tank is closed. The valve between columns 2 and 3 closes the inlet to column 3 and opens the inlet to detector/collecting tank (valve position II). The temperature of column 2 is kept at 58° C. Column 1 is heated to a temperature that is above the melting temperature of the wild type-oligonucleotide hybrid. Then, buffer is pumped through the system. The bound DNA is eluted from column 1.

In column 2, the wild type DNA hybridizes with the oligonucleotide shown on the right-hand side. If a point mutation is present in the DNA section of the mutated allele, which is complementary to the bound oligonucleotide, the mutated allele will not be bound and will instead pass to the detector and collecting tank. If the point mutation is present in another DNA section, the mutated allele will also be bound. Thereafter, the valve position between columns 2 and 3 is changed such that the inlet to column 3 opens and the inlet to detector/collecting tank is closed (valve position III). The sample DNA is eluted by heating as before, and is fed into column 3.

Figure 3:
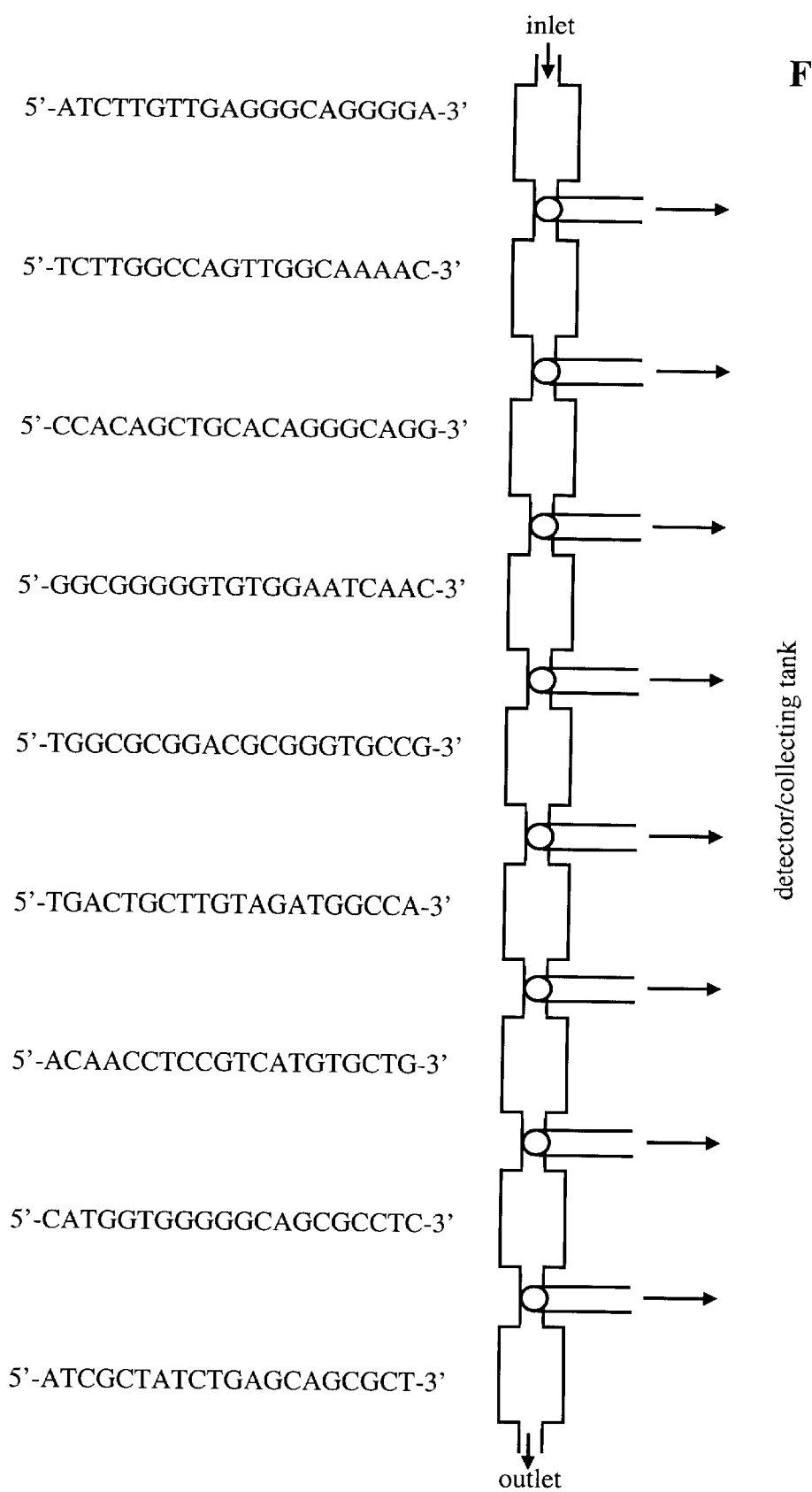
FIG. 3 shows a schematic flow-chart for separation of mutated p53 alleles from p53 wild type alleles using separation chambers arranged in series, with each chamber charged with carrier-bound oligonucleotides.

The procedure is continued correspondingly until all columns have been passed through. A separation means is shown in FIG. 3, which enables the detection of point mutations throughout exon 5 of the p53 gene. The bound oligonucleotides shown on the left-hand side cover the entire region of the sense strand of exon 5 of the p53 gene.

EXAMPLE 3.

Analysis of Pancreatic Mutations Associated with Pancreatic Carcinoma

Figure 5:
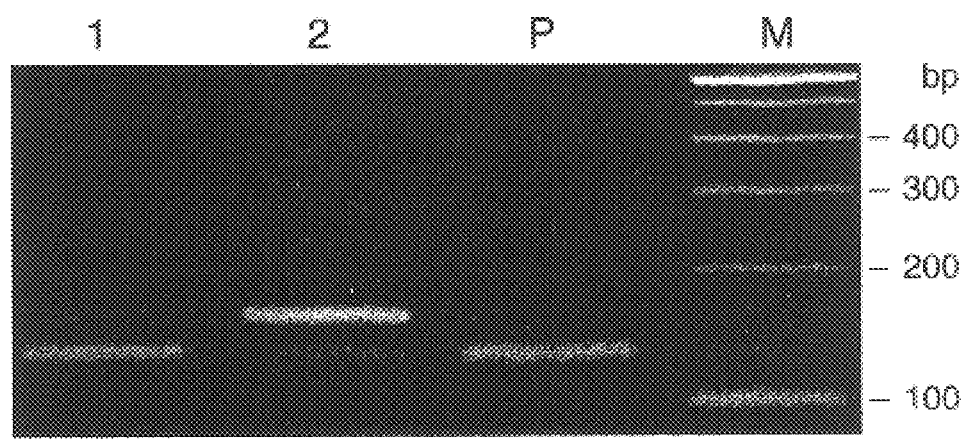
FIG. 5 shows an electrophoresis gel to analyze the products of subtractive iterative PCR amplification and removal of wild-type alleles to enrich a mutant K-ras allele. The gel shows RFLP analysis of a 1:1000 mixture of mutant and wild type alleles.

For an evaluation of the siPCR assay, mutant DNA harboring a point mutation in codon 12 of the K-ras gene was used as a model system. A 1:1000 mixture of single-stranded mutant to wild-type K-ras alleles was loaded on a chromatographic device. A second PCR was performed on the eluted DNA; ssDNA was prepared and passed over an identical column. As shown in FIG. 5, only a faint band of the mutant allele was visible in the RFLP gel after the first separation step (Lane 1). In contrast, the mutant allele exhibited a stronger signal than the wild-type allele in the flow through collected after the second chromatographic run (Lane 2). The result was confirmed by DNA sequencing.

To illustrate the utility of a diagnostic siPCR process using biological samples, pancreatic juice examination samples were collected during routinely performed endoscopic retrograde cholangiopancreatography from patients who were clinically suspected of a pancreatic disease. The samples were analyzed applying the two-step siPCR protocol described above.

Figure 6:
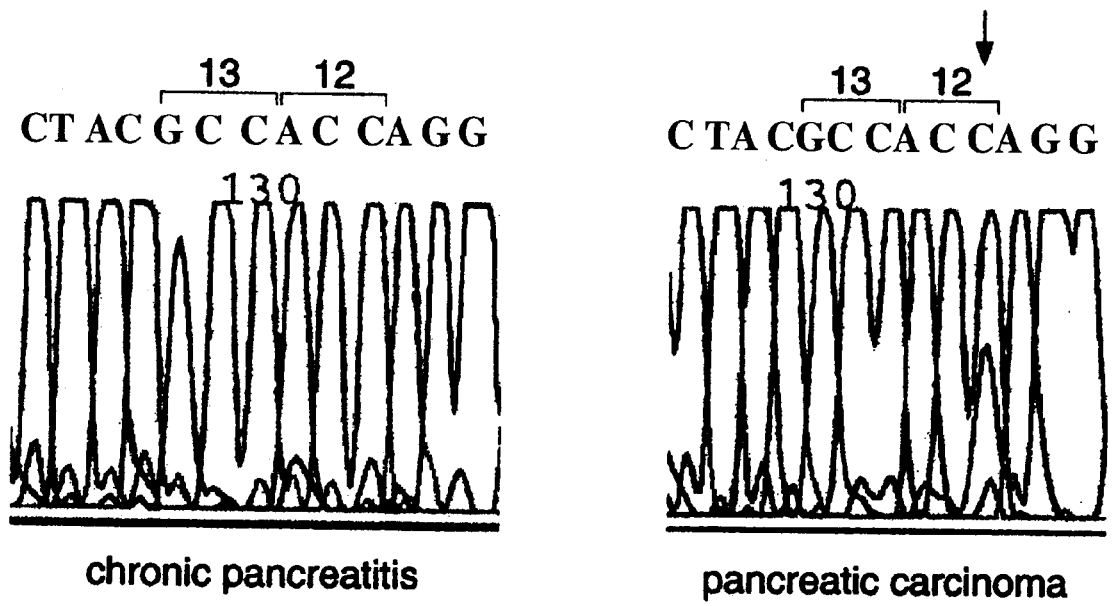
FIG. 6 shows the results of DNA sequencing (antisense) of the K-ras gene codons 12 and 13 in pancreatic juice after a two-step subtractive iterative PCR.

FIG. 6 shows typical examples of the outcome of a carcinoma and a chronic pancreatitis sample. An additional peak in the sequence analysis of the processed DNA indicates the presence of mutated K-ras alleles in samples obtained from carcinoma patients. The sample shown in the figure was analyzed in triplicate with each of the test results confirming the same specific base substitution. In contrast, no peak corresponding to a base substitution was identified between the wild-type sequence and the background signals of the sequence reaction in the case of a chronic pancreatitis sample. No mutations in codon 12 or 13 were present in eight of nine sampled from chronic pancreatitis patients (see Table I below). One sample contained a mutation at the first position of codon 12. All six samples from carcinoma patients contained DNA with a specific base substitution at the first or at the second position of codon 12. The base sequence of codon 13 was affected in any of the samples.

TABLE I

K-ras codons 12 and 13 of siPCR-processed DNA from pancreatic juice (wild-type sequence GCT GGC)

| Patient Number | Codons 12 and 13 |
|---|---|
| Chronic Pancreatitis | |
| 1 | GGT GGC |
| 2 | GGT GGC |

TABLE I-continued

K-ras codons 12 and 13 of siPCR-processed DNA from
pancreatic juice (wild-type sequence GCT GGC)

| Patient Number | Codons 12 and 13 |
|---|---|
| 3 | GGT GGC |
| 4 | CGT GGC |
| 5 | GGT GGC |
| 6 | GGT GGC |
| 7 | GGT GGC |
| 8 | GGT GGC |
| 9 | GGT GGC |
| Carcinoma | |
| 1 | CGT GGC |
| 2 | GCT GGC |
| 3 | CGT GGC |
| 4 | CGT GGC |
| 5 | GCT GGC |
| 6 | GTT GGC |

Patients and Sample Collection

About 1 mL secretin-stimulated pancreatic juice was collected during routinely performed endoscopic retrograde cholangiopancreatography from patients who were clinically suspected of a pancreatic disease. Samples were stored at −80° C. until DNA isolation was started. Diagnosis relied of the pathological findings, the results of diagnostic routines, and/or the clinical history of the patient.

Nucleic Acid Isolation

DNA was isolated from 200 µL of pancreatic juice using commercial DNA isolation columns (QIAamp DNA Blood Kit by Qiagen, Hilden, Germany). To establish the repetitive enrichment procedure, mutant DNA containing a G□T exchange at the first position in codon 12 of the K-ras gene was isolated from CaLu-I cells and mixed with wild-type DNA from MCF7 cells in defined mutant to wild-type ratios as described in Nollau P., Fischer C., Tschentscher P., and Wagener C. (1999). "Enrichment of mutant alleles by chromatographic removal of wild type alleles: a new principle for the detection of alleles with unknown point mutations at excess of wild type alleles." Clin. Chem. Lab. Med. 37:877–881.

Polymerase Chain Reactions and ssDNA Preparation

In the first PCR, 100 ng of the mutant K-ras DNA mixture or 5 µL of the DNA preparation from pancreatic juice was amplified in a 50 µL reaction with 0.3 µmol/L of primers Forward (5'-AACCTTATGTGTGACATGTTC-3') (SEQ ID NO. 6) and Reverse-1 (5'-ATGGTCAGAGAAACCTTTAT-3') (SEQ ID NO. 7) and 2.5 Units Pfu DNA polymerase at the conditions recommended by the supplier (Stratagene, Heidelberg, Germany). A second PCR was performed with 5 µL of the fourth flow-through fraction using the primers Forward and Reverse-2 (5'-Biotin-TCAAAGAATGGTCCTGCACC-3') (SEQ ID NO. 8). Polymerase chain reactions were performed on a thermal cycler (MJ Research, Biozym, Oldenhausen, Germany) with an initial denaturation at 94° C. for 5 min, 20 cycles of 1 min at 51° C. (first PCR) or 59° C. (second PCR), 1 min at 72° C., and 1 min at 94° C., followed by a final extension at 72° C. for 10 min. Single stranded DNA (ssDNA) was prepared and quantified as described (Nollau et al., 1999).

Column Preparation and Chromatographic Procedure

A column containing the oligonucleotide Capture (5'-Biotin-GCCTACGCCACCAGCTCCAA-3') (SEQ ID NO. 9) complementary to codons 9 to 15 of the K-ras wild-type allele was prepared and perfused with hybridization buffer as described (Nollau et al., 1999). After equilibration of the column at the calculated (Wetmur J. G. (1991), "DNA probes: applications of the principles of nucleic acid hybridization," Crit. Rev. Biochem. Mol. Biol. 26:227–259) temperature of 37° C., 1 µL ssDNA preparation diluted in 100 µL hybridization buffer was applied to the column. With a constant flow rate of 0.1 mL per min, the first milliliter of buffer was discarded and the following flow through was collected in 500-µL fractions. The non-bound fractions were desalted by spin cartridges (QIAquick PCR Purification, Qiagen) as recommended by the manufacturer.

RFLP Analysis and DNA Sequencing

For RFLP analysis, a PCR was performed as described with 10 L of the non-bound fraction and the primers RFLP Forward (5'-ACTGAATATAAACTTGTGGTAGTTGGACCT-3') (SEQ ID NO. 10) and Reverse-2. The primer RFLP Forward introduces an artificial BstNI restriction site at codon 12 allowing the detection of mutations by RFLP analysis as described (Nollau et al., 1999). PCR products were digested with the restriction enzyme BstNI as recommended by the supplier (NEB, Schwalbach/Taunus, Germany) and electrophoresed in 40 g/L low melting agarose gels. DNA sequencing was performed with the primer Reverse-2 by an ABI 373A DNA Sequencer (Applied Biosystems, Weiterstadt, Germany) using the manufacturer's Taq cycle sequencing protocol.

While the invention has been described herein with reference to various illustrative features, aspects and embodiments, it will be appreciated that the invention is susceptible of variations, modifications and other embodiments, other than those specifically shown and described. The invention is therefore to be broadly interpreted and construed as including all such alternative variations, modifications and other embodiments within its spirit and scope as hereinafter claimed.

What is claimed is:

1. A method for detecting mutated alleles in an excess of unmutated wild typed alleles, the method comprising:
    isolating from an examination sample a DNA sample comprising unmutated wild typed alleles and suspected mutated alleles, wherein the nucleotide sequence is known for the unmutated wild typed alleles;
    amplifying the DNA sample by PCR;
    introducing the amplified DNA sample into at least one chromatographic column wherein the at least one chromatographic column comprises at least one carrier-bound oligonucleotide sequence that either alone in a single column or in multiple columns is complementary to the entire region of interest of the unmutated wild type sequence suspected of including at least one point mutation, and wherein the wild type alleles bind to the carrier bound oligonucleotide DNA sequences and the mutated alleles do not bind under hybridizing conditions maintained at the melting temperature of the wild-type specific oligonucleotide and its complementary sequence or if the mutated alleles do bind they are eluted from the column before the wild type alleles when a buffer is added;
    and detecting the mutation in the mutated alleles eluted from the at least one chromatographic column.

2. The method according to claim 1, wherein the method is used to separate K-ras or p53 mutated alleles from an excess of unmutated K-ras or p53 wild type alleles, respectively.

3. The method according to claim 1, wherein the mutated alleles comprise at least one point mutation.

4. The method according to claim 1, wherein the multiple columns are arranged in parallel or in series for the separation process.

5. The method according to claim 1, wherein the at least one carrier bound oligonucleotides sequences comprise sense and/or anti-sense oligonucleotides that are complementary to the wild type alleles.

6. The method according to claim 1, wherein the carrier bound oligonucleotides sequences comprise from 16 to 20 base pairs.

7. The method according to claim 1, to be used for the diagnosis of genetic modification.

8. The method according to claim 1, to be used or the diagnosis of cancer.

9. A method for detecting K-ras or p53 mutated alleles in an excess of unmutated K-ras or p53 wild type alleles, comprising the steps of:
    a) obtaining an examination sample;
    b) isolating DNA from the examination sample;
    c) amplifying by PCR a sequence region that contains a target K-ras or p53 DNA sequence suspected of containing one or more mutations;
    d) converting the amplified K-ras or p53 DNA sequence region to single stranded DNA; and
    e) separating mutated single stranded DNA sequences from unmutated single stranded DNA sequences by introducing the single stranded DNA to at least one chromatographic column comprising at least one carrier-bound oligonucleotide, wherein the carrier bound oligonucleotides comprises a DNA sequence of 12 to 25 bases;

the at least one carrier bound oligonucleotide, has a sequence that either alone in a single column or in multiple columns is complementary to the entire region of interest in the unmutated wild type sequence with suspected point mutations;

and wherein the unmutated single stranded DNA sequences bind selectively to the carrier-bound oligonucleotide and the mutated single stranded DNA sequence do not bind under hybridizing conditions maintained at the melting temperature of the unmutated single stranded DNA sequence and its complementary sequence or the mutated single stranded DNA sequences are eluted from the column before the unmutated single stranded DNA sequences when a buffer is used; and f. detecting the mutation in the K-ras or p53 mutated alleles eluted from the at least one chromatographic column.

10. A method according to claim 9, wherein the mutated single stranded DNA sequences are selectively eluted from the column comprising the carrier-bound oligonucleotides.

11. A method according to claim 9, further comprising separating sense strands from the antisense strands after the amplified DNA sequence region is converted to single stranded DNA.

12. A method according to claim 11, wherein the sense strands are employed in the separation step.

13. A method according to claim 11, wherein the antisense strands are employed in the separation step.

14. A method according to claim 9, wherein the carrier bound oligonucleotide comprise at least one DNA sequence complementary to a sense strand and at least one DNA sequence complementary to an antisense strand of the amplified DNA sequence region.

15. A method according to claim 9, wherein the carrier bound oligonucleotide is bound to a carrier material that is selected from the group consisting of glasses, gel materials, and polymer materials.

16. A method according to claim 9, wherein the at least one carrier-bound oligonucleotides comprises a plurality of oligonucleotides having different sequences, and mutated single stranded DNA sequences are separated from unmutated single stranded DNA sequences by preferential binding of the unmutated single stranded DNA sequences to the different sequence oligonucleotides in series.

17. A method according to claim 9, wherein the at least one carrier-bound oligonucleotides comprises a plurality of oligonucleotides having different sequences in multiple, and mutated single stranded DNA sequences are separated from unmutated single stranded DNA sequences by preferential binding of the unmutated single stranded DNA sequences to the different sequence oligonucleotides configured in a parallel flow arrangement.

18. A method according to claim 9, further comprising at least one repetition of the sequential steps of:

amplifying by PCR the mutated single stranded DNA sequences obtained by separation from unmutated single stranded DNA sequences; and subjecting the amplified mutated single stranded DNA sequences to the separation step of step (e) to remove residual unmutated single stranded DNA sequences, where the separation step employs preferential binding of the unmutated single stranded DNA sequences to one or more carrier-bound oligonucleotides.

19. A method according to claim 17, further comprising at least one repetition of the sequential steps of:

amplifying the mutated single stranded DNA sequences obtained by separation from unmutated single stranded DNA sequences; subjecting the amplified mutated single stranded DNA sequences to the separation step of step (e) to remove residual unmutated single stranded DNA sequences, where the separation step employs preferential binding of the unmutated single stranded DNA sequences to one or more carrier-bound oligonucleotides.

20. A method according to claim 19, wherein the at least one repeated separation step(s) of step (e) employs a plurality of carrier-bound oligonucleotides in multiple columns arranged in parallel or in series for the separation process.

21. A method according to claim 19, wherein the at least one repeated separation step(s) employs a single oligonucleotide.

22. A method according to claim 9, further comprising identifying a genetic modification in the mutated DNA sequences.

23. A method according to claim 9, wherein the examination sample comprises a material selected from the group consisting of stool, sputum, bronchial lavage, urine, tissue biopsy material, saliva, and smear material.

24. A method according to claim 9, wherein the examination sample comprises stool from a patient suspected of having colorectal carcinoma.

25. A method according to claim 9, wherein the examination sample comprises a sputum sample or a bronchial lavage sample from a patient suspected of having bronchial carcinoma.

26. A method according to claim 9, wherein the examination sample comprises urine from a patient suspected of having bladder carcinoma.

27. A method according to claim 9, wherein the examination sample comprises a tissue biopsy sample.

* * * * *

UNITED STATES PATENT AND TRADEMARK OFFICE
CERTIFICATE OF CORRECTION

PATENT NO. : 6,599,704 B2  Page 1 of 1
DATED : July 29, 2003
INVENTOR(S) : Christoph Wagener It is certified that error appears in the above-identified patent and that said Letters Patent is hereby corrected as shown below:

Column 10,
Line 55, "anti-sense sense" should be -- anti-sense --

Column 12,
Line 50, "sampled" should be -- samples --
Line 55, "was affected" should be -- was not affected --

Column 13,
Line 30, "of the pathological findings" should be -- on the pathological findings --
Line 37, "G=T" should be -- G→T --
Line 54, "5'-ATGGTCAGAGAAACCTTTAT" should be
-- 5'-Biotin-ATGGTCAGAGAAACCTTTAT --

Signed and Sealed this

Sixteenth Day of December, 2003

JAMES E. ROGAN
*Director of the United States Patent and Trademark Office*

SEQUENCE LISTING

<160> NUMBER OF SEQ ID NOS: 10

<210> SEQ ID NO 1
<211> LENGTH: 26
<212> TYPE: DNA

```
<213> ORGANISM: Artificial Sequence
<220> FEATURE:
<223> OTHER INFORMATION: Sense Primer

<400> SEQUENCE: 1
gtattaacct tatgtgtgac atgttc                                              26

<210> SEQ ID NO 2
<211> LENGTH: 20
<212> TYPE: DNA
<213> ORGANISM: Artificial Sequence
<220> FEATURE:
<223> OTHER INFORMATION: Antisense Primer

<400> SEQUENCE: 2
tcaaagaatg gtcctgcacc                                                     20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
gcctacgcca ccagctccaa                                                     20

<210> SEQ ID NO 4
<211> LENGTH: 20
<212> TYPE: DNA
<213> ORGANISM: Artificial Sequence
<220> FEATURE:
<223> OTHER INFORMATION: Sense Primer

<400> SEQUENCE: 4
tttccactct gtctccttcc                                                     20

<210> SEQ ID NO 5
<211> LENGTH: 20
<212> TYPE: DNA
<213> ORGANISM: Artificial Sequence
<220> FEATURE:
<223> OTHER INFORMATION: Anti-sense Primer

<400> SEQUENCE: 5
aaccagccct gtcgtctctc                                                     20

<210> SEQ ID NO 6
<211> LENGTH: 21
<212> TYPE: DNA
<213> ORGANISM: Artificial Sequence
<220> FEATURE:
<223> OTHER INFORMATION: Primer Forward

<400> SEQUENCE: 6
aaccttatgt gtgacatgtt c                                                   21

<210> SEQ ID NO 7
<211> LENGTH: 20
<212> TYPE: DNA
<213> ORGANISM: Artificial Sequence
<220> FEATURE:
<223> OTHER INFORMATION: Primer Reverse-1
<221> NAME/KEY: Biotin
<222> LOCATION: (1)..(1)

<400> SEQUENCE: 7
```

```
atggtcagag aaacctttat                                              20

<210> SEQ ID NO 8
<211> LENGTH: 20
<212> TYPE: DNA
<213> ORGANISM: Artificial Sequence
<220> FEATURE:
<223> OTHER INFORMATION: Primer Reverse-2
<221> NAME/KEY: Biotin
<222> LOCATION: (1)..(1)

<400> SEQUENCE: 8
tcaaagaatg gtcctgcacc                                              20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide Capture
<221> NAME/KEY: Biotin
<222> LOCATION: (1)..(1)

<400> SEQUENCE: 9
gcctacgcca ccagctccaa                                              20

<210> SEQ ID NO 10
<211> LENGTH: 30
<212> TYPE: DNA
<213> ORGANISM: Artificial Sequence
<220> FEATURE:
<223> OTHER INFORMATION: Primer RFLP Forward

<400> SEQUENCE: 10
actgaatata aacttgtggt agttggacct                                   30
```